United States Patent
Sanderson et al.

[11] Patent Number: 6,117,888
[45] Date of Patent: Sep. 12, 2000

[54] THROMBIN INHIBITORS

[75] Inventors: Philip E. Sanderson, Philadelphia; Kellie Cutrona, Harleysville, both of Pa.

[73] Assignee: Merck & Co., Inc., Rahway, N.J.

[21] Appl. No.: 09/407,830

[22] Filed: Sep. 28, 1999

Related U.S. Application Data

[60] Provisional application No. 60/102,021, Sep. 28, 1998.

[51] Int. Cl.$^7$ ..................... C07D 401/12; A61K 31/4412
[52] U.S. Cl. .................. 514/333; 546/256; 546/194; 546/261; 546/193; 514/318; 514/335
[58] Field of Search ..................... 546/256, 193, 546/194, 261; 514/333, 318, 335

[56] References Cited

U.S. PATENT DOCUMENTS

| | | |
|---|---|---|
| 5,260,307 | 11/1993 | Ackermann et al. . |
| 5,405,854 | 4/1995 | Ackermann et al. . |
| 5,459,142 | 10/1995 | Tone et al. . |
| 5,510,369 | 4/1996 | Lumma et al. . |
| 5,744,486 | 4/1998 | Sanderson et al. . |
| 5,866,573 | 2/1999 | Sanderson et al. . |

FOREIGN PATENT DOCUMENTS

| | | |
|---|---|---|
| 262096 | 9/1987 | European Pat. Off. . |
| 509769 | 4/1992 | European Pat. Off. . |
| WO 9831670 | 7/1998 | European Pat. Off. . |
| WO 94/25051 | 10/1994 | WIPO . |
| WO 96/11697 | 4/1996 | WIPO . |
| WO 96/31504 | 10/1996 | WIPO . |
| WO 96/32110 | 10/1996 | WIPO . |
| WO 97/01338 | 1/1997 | WIPO . |
| WO 97/40024 | 10/1997 | WIPO . |

OTHER PUBLICATIONS

Bernstein, Peter R. et al, "Nonpeptidic Inhibitors of Human Leukocyte Elastase . . .".*J. Med. Chem.*, vol. 37, pp. 3313–3326 (1994).

Sanderson, P. E., et al., "Preparation Of 3–Amino–2–Pyrazinone–1–Acetamide Derivatives As Thrombin Inhibitors," *Chem. Abstr.*, vol. 128, No. 3, pp. 532 (1998).

Sanderson, et al., Preparation of Aminopyridones as Thrombin Inhibitors, Database Caplus on STN, No. 129:136100 (1998).

*Primary Examiner*—Jane Fan
*Attorney, Agent, or Firm*—Richard S. Parr; Melvin Winokur

[57] ABSTRACT

Compounds of the invention are useful in inhibiting thrombin and associated thrombotic occlusions having the following structure:

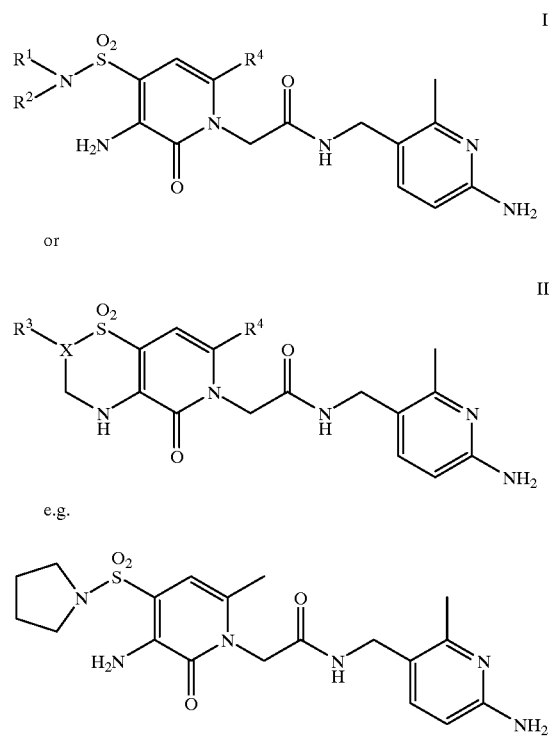

6 Claims, No Drawings

THROMBIN INHIBITORS

This is a non-provisional application of provisional application No. 60/102,021, filed Sep. 28, 1998.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., *J. Med. Chem.*, Vol. 37, pages 1259–1261 (1994) describes orally active, non-peptidic inhibitors of human leukocyte elastase which contain trifluoromethylketone and pyridinone moieties.

H. Mack et al., *J. Enzyme Inhibition*, Vol. 9, pages 73–86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention, useful as thrombin inhibitors and having therapeutic value in for example, preventing coronary artery disease, have the following structure (formula I or II):

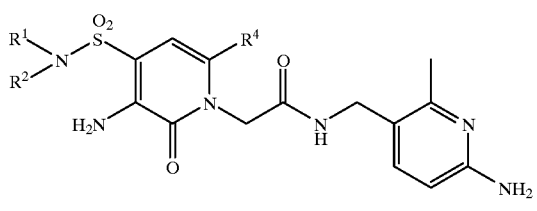

or

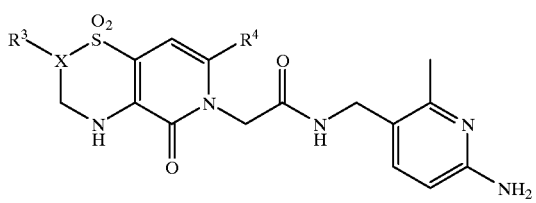

or a pharmaceutically acceptable salt thereof, wherein

X is N or CH;

$R^1$ and $R^2$ are independently selected from
  hydrogen,
  -phenyl, unsubstituted or substituted with one or more of
    $C_{1-4}$ alkyl,
    $C_{1-4}$ alkoxy,
    halogen,
    hydroxy,
    COOH, or
    $CONH_2$,
  naphthyl,
  biphenyl,
  a 5- to 7-membered mono- or a 9- to 10-membered bicyclic heterocyclic ring which can be saturated or unsaturated, and which contains from one to four heteroatoms selected from the group consisting of N, O and S,
  —$C_{1-7}$ alkyl, unsubstituted or substituted with one or more of
    hydroxy,
    COOH,
    amino,
    aryl,
    $C_{3-7}$ cycloalkyl,
    heteroaryl, or
    heterocycloalkyl,
  —$CF_3$
  $C_{3-7}$ cycloalkyl,
  $C_{7-12}$ bicyclic alkyl, or
  $C_{10-16}$ tricyclic alkyl;
or $R^1$ and $R^2$ together with the nitrogen to which they are bound form a 5- or 6-membered ring containing 1 nitrogen atom;

$R^3$ is hydrogen,
  -phenyl, unsubstituted or substituted with one or more of
    $C_{1-4}$ alkyl,
    $C_{1-4}$ alkoxy,
    halogen,
    hydroxy, COOH, or
CONH$_2$,
naphthyl,
biphenyl,
a 5- to 7-membered mono- or a 9- to 10-membered bicyclic heterocyclic ring which can be saturated or unsaturated, and which contains from one to four heteroatoms selected from the group consisting of N, O and S,
—C$_{1-7}$ alkyl, unsubstituted or substituted with one or more of
hydroxy,
COOH,
amino,
aryl,
C$_{3-7}$ cycloalkyl,
heteroaryl, or
heterocycloalkyl,
—CF$_3$
C$_{3-7}$ cycloalkyl,
C$_{7-12}$ bicyclic alkyl, or
C$_{10-16}$ tricyclic alkyl; and
R$^4$ is hydrogen,
—C$_{1-4}$ alkyl,
C$_{3-7}$ cycloalkyl, or
trifluoromethyl.

In one class of compounds, R$^1$ is hydrogen; R$^2$ is —C$_{3-7}$ cycloalkyl or —CH$_2$ C$_{3-7}$ cycloalkyl; or R$^1$ and R$^2$ form a 5- or 6-membered ring containing 1 nitrogen atom; R$^3$ is hydrogen, aryl, —C$_{3-7}$ cycloalkyl or —CH$_2$C$_{3-7}$ cycloalkyl; and R$^4$ is hydrogen, —C$_{1-4}$ alkyl, C$_{3-7}$ cycloalkyl or trifluoromethyl.

Specific examples are shown below in Table 1. Inhibitory activity of compounds of the invention is represented by "*", indicating Ki greater than or equal to 5 nM, or "**", indicating Ki less than 5 nM. Values are as determined according to the in vivo assay described later in the specification.

TABLE 1

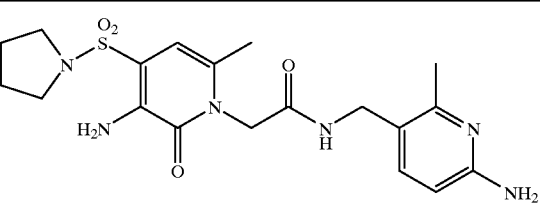

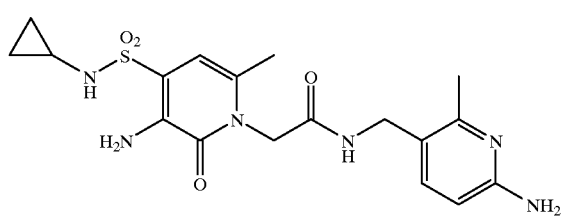

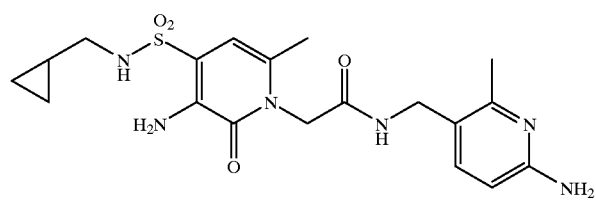

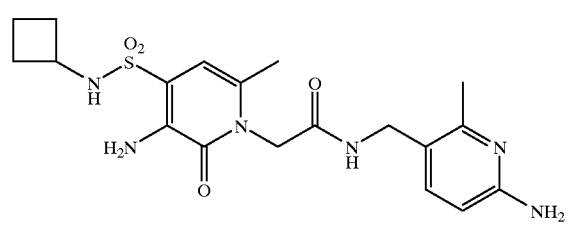

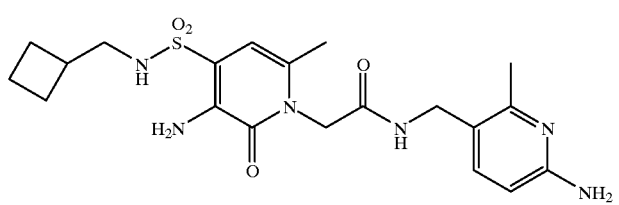

TABLE 1-continued

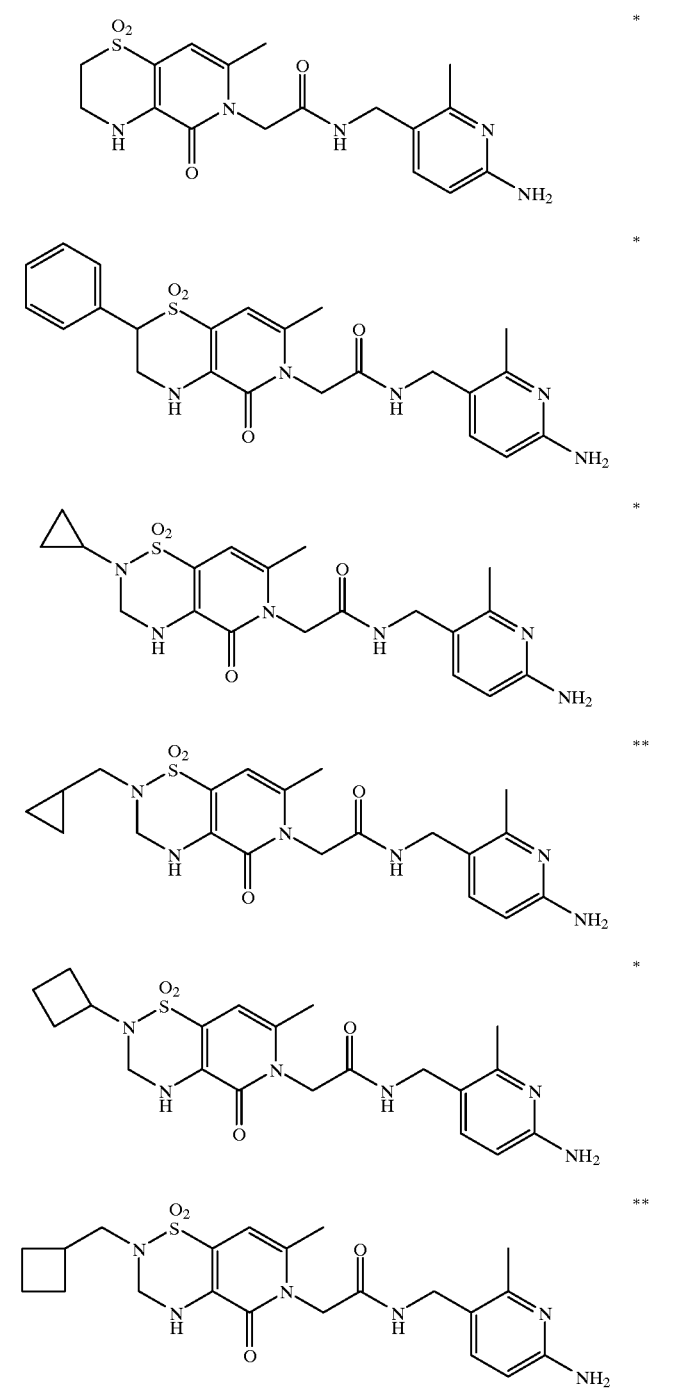

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence.

Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethyl-bicyclo[2.2.1]heptyl (bornyl), and the like. The term "$C_{10-16}$ tricyclic alkyl" is intended to include cyclic ring systems having 10–16 carbon atoms arranged in cyclic relationship.

The term "aryl" as used herein except where noted, represents a stable 6- to 10-membered mono- or bicyclic ring system. The aryl ring can be unsubstituted or substituted with one or more of $C_{1-4}$ lower alkyl; hydroxy; alkoxy; halogen; amino. Examples of "aryl" groups include phenyl and naphthyl.

The term "heterocycle" or "heterocyclic ring", as used herein except where noted, represents a stable 5- to 7-membered mono- or bicyclic or stable 9- to 10-membered bicyclic heterocyclic ring system any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Bicyclic unsaturated ring systems include bicyclic ring systems which may be partially unsaturated or fully unsaturated. Partially unsaturated bicyclic ring systems include, for example, cyclopentenopyridinyl, benzodioxan, methylenedioxyphenyl groups. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiophenyl, oxazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl. Unsaturated heterocyclic rings may also be referred to hereinafter as "heteroaryl" rings.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Some abbreviations that may appear in this application are as follows.

| ABBREVIATIONS | |
|---|---|
| Designation | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |
| HBT (HOBT or HOBt) | 1-hydroxybenzotriazole hydrate |
| Designation | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chlorid |
| EDC | 1-ethyl-3-(3-dimethylaminopropyl) carbodiimide hydrochloride |
| | Other |
| (BOC)$_2$O (BOC$_2$O) | di-t-butyl dicarbonate |
| n-Bu$_4$N+F– | tetrabutyl ammonium fluoride |
| nBuLi (n-Buli) | n-butyllithium |
| DMF | dimethylformamide |
| Et$_3$N (TEA) | triethylamine |
| EtOAc | ethyl acetate |
| TFA | trifluoroacetic acid |
| DMAP | dimethylaminopyridine |
| DME | dimethoxyethane |
| NMM | N-methylmorpholine |
| DPPA | diphenylphosphoryl azide |
| THF | tetrahydrofuran |
| DIPEA | diisopropylethylamine |
| | Amino Acid |
| Ile | Isoleucine |
| Phe | Phenylalanine |
| Pro | Proline |
| Ala | Alanine |
| Val | Valine |

IN VITRO ASSAY FOR DETERMINING PROTEINASE INHIBITION

Assays of human α-thrombin and human trypsin were performed by the methods substantially as described in *Thrombosis Research,* Issue No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM CaCl$_2$. In assays wherein rates of hydrolysis of a p-nitroanilide (pna) substrate were determined, a Thermomax 96-well plate reader was used was used to measure (at 405 nm) the time dependent appearance of p-nitroaniline. sar-PR-pna was used to assay human α-thrombin (K$_m$=125 μM) and bovine trypsin (K$_m$=125 μM). p-Nitroanilide substrate concentration was determined from measurements of absorbance at 342 nm using an extinction coefficient of 8270 cm$^{-1}$M$^{-1}$.

In certain studies with potent inhibitors (K$_i$<10 nM) where the degree of inhibition of thrombin was high, a more sensitive activity assay was employed. In this assay the rate of thrombin catalyzed hydrolysis of the fluorogenic substrate Z-GPR-afc (K$_m$=27 μM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≦0.1 K$_m$ into a solution containing enzyme or enzyme equilibrated with inhibitor. Times required to achieve equilibration between enzyme and inhibitor were determined in control experiments. Initial velocities of product formation in the absence (V$_o$) or presence of inhibitor (V$_i$) were measured. Assuming competitive inhibition, and that unity is negligible compared K$_m$/[S], [I]/e, and [I]/e (where [S], [I], and e respectively represent the total concentrations, of substrate, inhibitor and enzyme), the equilibrium constant (K$_i$) for dissociation of the inhibitor from the enzyme can be obtained from the dependence of V$_o$/V$_i$ on [I] shown in equation 1.

$$V_o/V_i=1+[I]/K_i \quad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The compounds of the invention are selective compounds, as evidenced by their inhibitory activity against human trypsin (represented by Ki), which is at least 1000 nM.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Typical uncoated tablet cores suitable for administration of thrombin inhibitors are comprised of, but not limited to, the following amounts of standard ingredients:

| Excipient | General Range (%) | Preferred Range (%) | Most Preferred Range (%) |
|---|---|---|---|
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including anti-hypercholesterolemics (e.g. HMG CoA reductase inhibitors such as lovastatin or simvastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The following synthetic methods can be used to prepare the compounds of the present invention:

METHOD 1

As exemplified by Example 3.

Starting 2,4-dihydroxy-3-nitropyridine is reacted with a dehydrating chloride source, for example phosphorous oxychloride, in Step A to give the 4-chloropyridine. This is alkylated in Step B with an acetate equivalent such as ethylbromoacetate. The 4-chloropyridinone is reacted in Step C with 2-mercaptobenzothiazole in the presence of an amine base such as triethylamine, in ethanol. The nitro group is reduced by catalytic hydrogenation over palladium on carbon in ethyl acetate in Step D. The amino group is protected as its bis-BOC derivative using DMAP as a catalyst in Step E and the thioether is oxidised with potassium permanganate in aqueous acetic acid to give the sulfone in Step F. The sulfone is reduced in Step G to the sulfinate salt using zinc in ethanolic acetic acid and the sulfinate is then reacted with NCS in Step H to give the sulfonyl chloride. In Step I, reaction of the sulfonyl chloride with an amine in the presence of a base such as NMM gives the sulfonamide and the BOC groups are removed in Step J using a strong acid such as anhydrous HCl in ethyl acetate. The ester is then hydrolysed with lithium hydroxide in Step K and the carboxylic acid is coupled to the appropriate amine in Step L to give the final product.

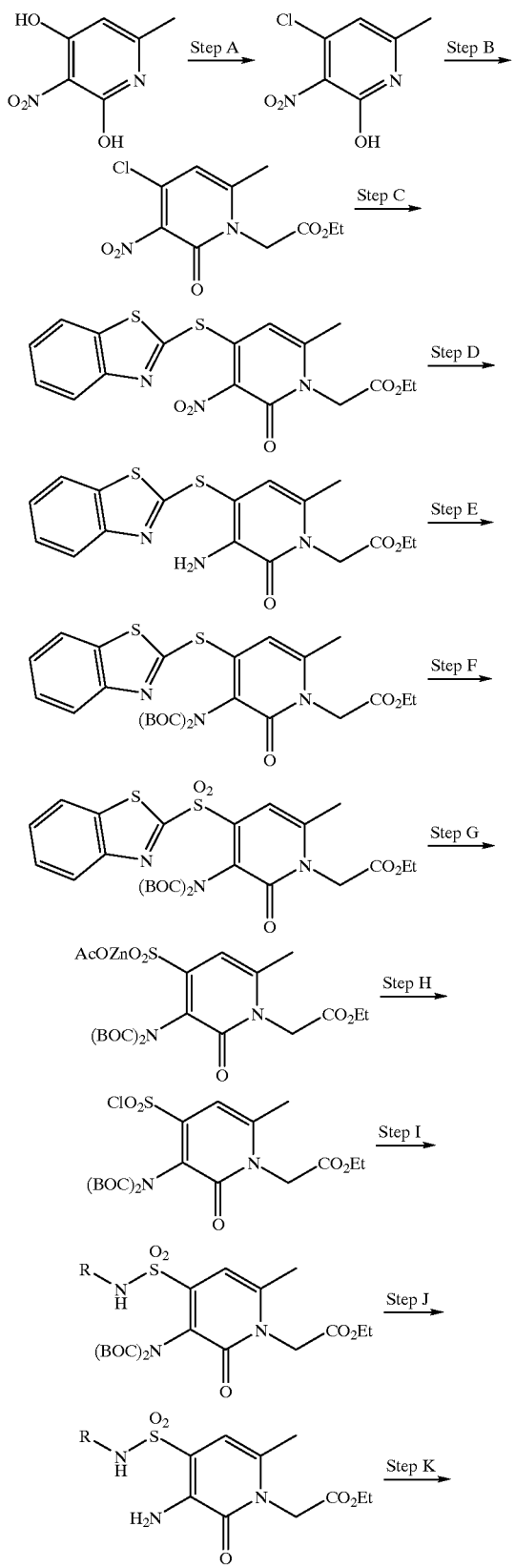

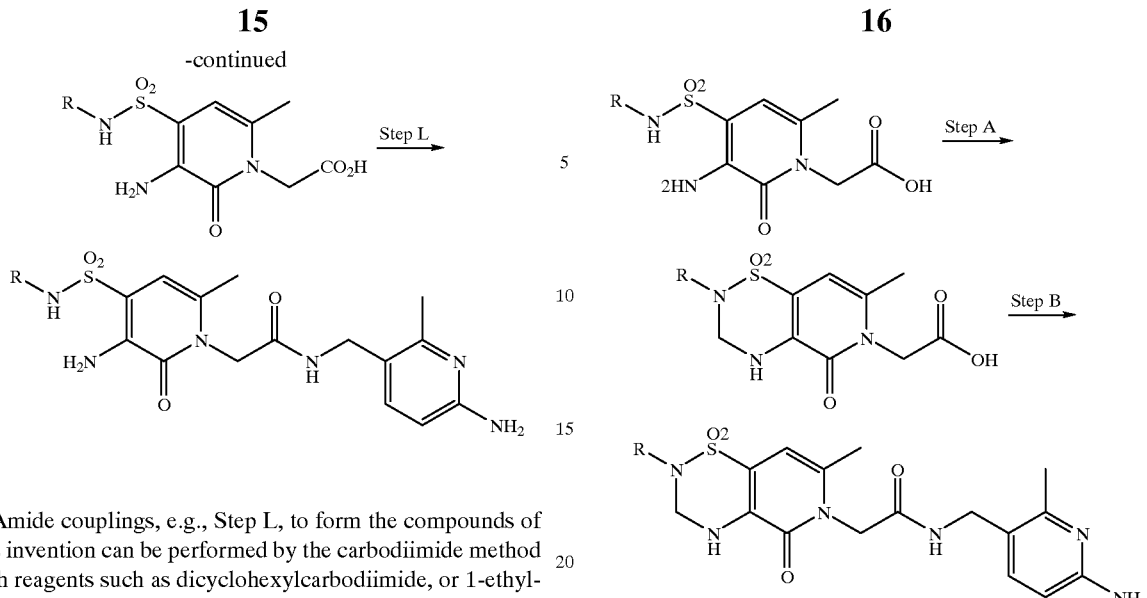

Amide couplings, e.g., Step L, to form the compounds of this invention can be performed by the carbodiimide method with reagents such as dicyclohexylcarbodiimide, or 1-ethyl-3-(3-dimethyl-aminopropyl) carbodiimide. Other methods of forming the amide or peptide bond include, but are not limited to the synthetic routes via an acid chloride, azide, mixed anhydride or activated ester. Typically, solution phase amide couplings are performed, but solid-phase synthesis by classical Merrifield techniques may be employed instead. The addition and removal of one or more protecting groups is also typical practice. Obvious variations and modifications of the method to produce similar and obvious varients thereof, will be apparent to one skilled in the art.

METHOD 2

As exemplified by Example 4.

The product of Method 1, Step L, is reacted with excess formaldehyde and the crude reaction product was hydrolysed in aqueous acid to give the final product.

METHOD 3

As exemplified by Example 8.

The product of Method 1, Step K is reacted with excess formaldehyde in Step A and the carboxylic acid then coupled to the appropriate amine in Step B to give the final product.

METHOD 4

As exemplified by Example 1.

The product of Method 1, Step B, is reacted with a 2-mercaptoethanol in Step A. The thioether is then reacted with dehydrating chloride source such as phosphorous pentachloride to give the chloroethyl derivative in Step B. The thioether is then oxidised to the sulfone in Step C using a reagent such as mCPBA or OXONE®, and the nitro group is reduced in Step D by catalytic hydrogenation. The amine is then cyclised in Step E by heating a solution of the amine in the presence of a base such as potassium carbonate. The ester is then hydrolysed with lithium hydroxide in Step F and the carboxylic acid is coupled to the appropriate amine in Step G which is then deprotected in Step H using a strong acid to give the final product.

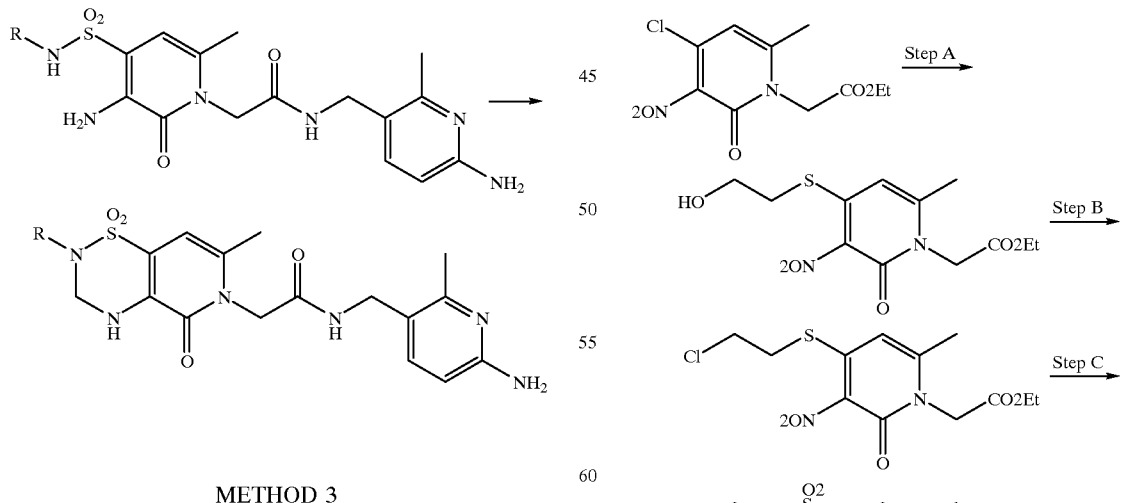

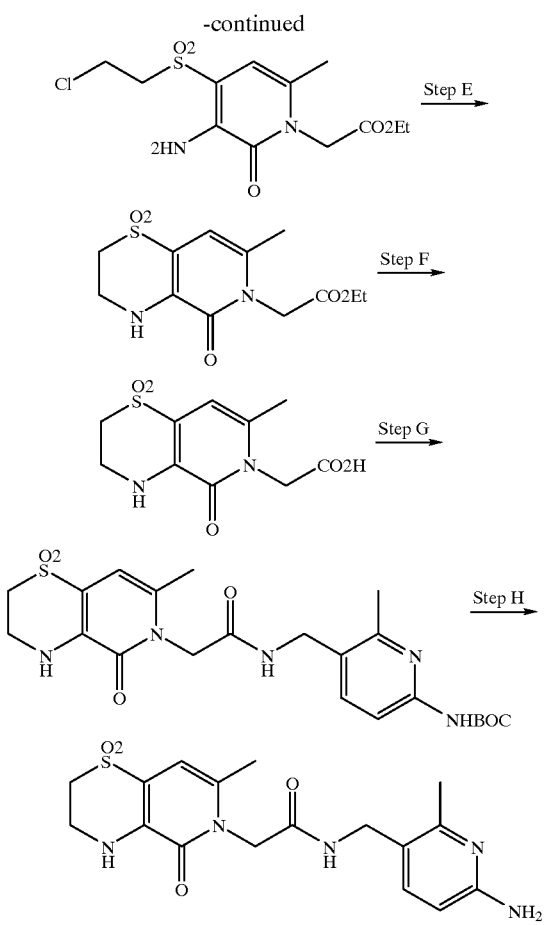

Modifications of this method will allow different R³ groups contemplated by the broad claim below to be present by the use of the appropriate reagent or the appropriate substituted starting material in the indicated synthetic step. Obvious variations and modifications of the method to produce similar and obvious varients thereof, will be apparent to one skilled in the art.

The following examples are illustrative of the invention as contemplated by the inventors and should not be construed as being limits on the scope or spirit of the instant invention.

EXAMPLE 1

Preparation of 6-(2-Amino-6-methyl-5-methylenecarboxamido-methylpyridinyl)-7-methyl-5-oxo-3,4,5,6-tetrahydropyrido-[4,3-b]-1,4-thiazine-1,1-dioxide

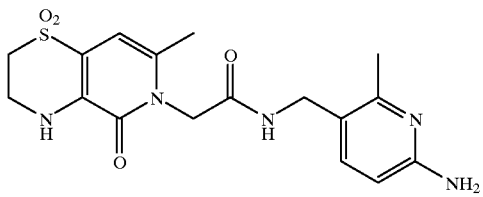

Step A: 1-Ethyloxycarbonylmethyl-4-(2-hydroxyethylthio)-6-methyl-3-nitro-2-pyridinone 2-Mercaptoethanol (0.168 mL, 2.4 mmol) was added to a stirred mixture of 4-chloro-1-ethyloxycarbonylmethyl-6-methyl-3-nitro-2-pyridinone (the product of Example 3, Step B, 549 mg, 2.0 mmol) and triethylamine (0.613 mL, 4.4 mmol) in ethanol (4 mL) and the mixture was heated to reflux for 15 min. The reaction was cooled and evaporated to a solid which was purified by flash column chromatography on silica gel (eluting with ethyl acetate), to give the title compound as a pale yellow crystalline solid:

NMR (CDCl₃); d 1.31 (t, 3H), 2.05 (br t, 1H), 2.37 (s, 3H), 3.18 (t, 2H), 3.93 (br q, 2H), 4.26 (q, 2H), 4.80 (s, 2H), 6.21 (s, 1H).

Step B: 4-(2-Chloroethylthio)-1-ethyloxycarbonylmethyl-6-methyl-3-nitro-2-pyridinone Phosphorus pentachloride (229 mg, 1.1 mmol) was added to a stirred solution of 1-ethyloxycarbonylmethyl-4-(2-hydroxyethylthio)-6-methyl-3-nitro-2-pyridinone (316 mg, 1.0 mmol) in methylene chloride (5 mL). After 15 min the reaction was diluted with methylene chloride and was washed with water, dried (Na₂SO₄) and evaporated to give the title compound as a yellow crystalline solid:

NMR (CDCl₃); d 1.31 (t, 3H), 2.40 (s, 3H), 3.32 (t, 2H), 3.70 (t, 2H), 4.26 (q, 2H), 4.81 (s, 2H), 6.01 (s, 1H).

Step C: 4-(2-Chloroethylsulfonyl)-1-ethyloxycarbonylmethyl-6-methyl-3-nitro-2-pyridinone A mixture of OXONE® (922 mg, 1.5 mmol) and 4-(2-chloroethylthio)-1-ethyloxycarbonylmethyl-6-methyl-3-nitro-2-pyridinone (168 mg, 0.5 mmol) in 1:1 methanol/water (8 mL) was stirred for 8 days. The reaction was partitioned between ethyl acetate and water, and the organc layer was dried (Na₂SO₄) and evaporated to give the title compound as a solid:

NMR (CDCl₃); d 1.32 (t, 3H), 2.48 (s, 3H), 3.88 (m, 4H), 4.28 (q, 2H), 4.88 (s, 2H), 6.59 (s, 1H).

Step D: 3-Amino-4-(2-chloroethylsulfonyl)-1-ethyloxycarbonylmethyl-6-methyl-2-pyridinone A mixture of platinum (IV) oxide (24 mg) and 4-(2-chloroethylsulfonyl)-1-ethyloxycarbonylmethyl-6-methyl-3-nitro-2-pyridinone (120 mg, 0.33 mmol) in ethanol (3.0 mL) was stirred under hydrogen for 16 h. The reaction was filtered through celite and evaporated to give the title compound as a glass:

NMR (CDCl₃); d 1.31 (t, 3H), 2.44 (s, 3H), 3.57 (t, 2H), 3.80 (t, 2H), 4.26 (q, 2H), 4.79 (s, 2H), 5.90 (br s, 2H), 6.23 (s, 1H).

Step E: 6-Ethyloxycarbonylmethyl-7-methyl-5-oxo-3,4,5,6-tetrahydropyrido-[4,3-b]-1,4-thiazine-1,1-dioxide A mixture of potassium carbonate (45 mg) and 3-amino-4-(2-chloroethylsulfonyl)-1-ethyloxycarbonylmethyl-6-methyl-2-pyridinone (120 mg, 0.33 mmol) in dimethyl acetamide (1.0 mL) was stirred at 160° C. for 1 h. The reaction mixture was cooled and partitioned between ethyl acetate and dilute HCl. The organic layer was washed with brine, dried (Na₂SO₄) and evaporated to a semi-solid. The crude product was purified by flash column chromatography on silica gel (70–100% ethyl acetate/hexanes gradient) to give the title compound as a colorless crystalline solid:

NMR (DMSO-d₆); d 1.21 (t, 3H), 2.21 (s, 3H), 3.36 (m, 2H), 3.74 (m, 2H), 4.16 (q, 2H), 4.79 (s, 2H), 6.28 (s, 1H), 6.97 (br s, 1H).

Steps F–H: 6-(2-Amino-6-methyl-5-methylenecarboxamido-methylpyridinyl)-7-methyl-5-oxo-3,4,5,6-tetrahydropyrido-[4,3-b]-1,4-thiazine-1,1-dioxide A mixture of lithium hydroxide monohydrate (21 mg) and 6-ethyloxycarbonylmethyl-7-methyl-5-oxo-3,4,5,6- tetrahydropyrido-[4,3-b]-1,4-thiazine-1,1-dioxide (25.3 mg, 0.084 mmol) in 1:1:1 methanol/THF/water (1.5 mL) was stirred for 64 h. 1M HCl solution (1 mL) was added and the solution was evaporated in vacuo to a solid. EDC.HCl (20.9 mg, 0.109 mmol) was add to a stirred solution of this material, HOBT (14.7 mg, 0.109 mmol), 5-aminomethyl-2-t-butoxycarbonylamino-6-methylpyridine) (20.0 mg, 0.084 mmol) and NMM (0.0212 mL, 0.193 mmol) in DMF (0.4 mL). After 16 h, the reaction was partitioned between ethyl acetate and water. The organic layer was washed with dilute citric acid solution and brine, dried ($Na_2SO_4$) and evaporated to a glass. The crude product was purified by flash column chromatography on silica gel (0–10% ethanol/ethyl acetate gradient) to give a glass. HCl gas was bubbled through a stirred mixture of this material and ethyl acetate (5 mL) for 15 min at 0° C. After a further 1 h at rt, the mixture was degassed with nitrogen for 10 min then was filtered through a cotton wool plug, washing with ethyl acetate. The solids were dissolved in methanol and evaporated to a tan solid. This was heated to reflux as a suspension in ethyl acetate (2 mL), cooled and collected by filtration to give the hydrochloride salt of the title compound as a tan solid;

NMR ($D_2O$); d 2.16 (s, 3H), 2.33 (s, 3H), 3.43 (m, 2H), 3.86 (m, 2H), 4.23 (s, 2H), 6.41 (s, 1H), 6.64 (d, 1H) 7.58 (d, 1H).

EXAMPLE 2

Preparation of 6-(2-Amino-6-methyl-5-methylenecarboxamido-methylpyridinyl)-7-methyl-5-oxo-2[RS]-phenyl-3,4,5,6-tetrahydropyrido-[4,3-b]-1,4-thiazine-1,1-dioxide

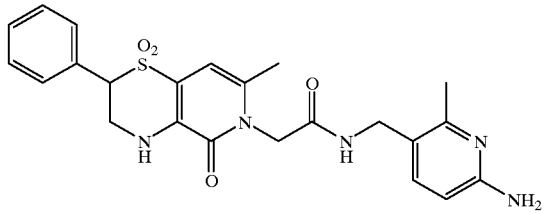

The TFA salt of the title compound was prepared from [RS]-1-phenyl-2-mercaptoethanol using the procedures of Example 1, Steps A–F followed by hydrolysis and coupling to 2-amino-5-aminomethyl-6-methylpyridine bis HCl salt using the procedure of Example 3, Steps K and L followed by purification by preparative HPLC (acetonitrile/0.1% aqueous TFA gradient), as a glass; HRMS (FAB) $C_{23}H_{26}N_5O_4S$ calcd. 468.1706 $(M+1)^+$. Found: 468.1709.

EXAMPLE 3

Preparation of 3-amino-1-(2-amino-6-methyl-5-methylenecarbox-amidomethylpyridinyl)-4-(N-cyclobutylmethylsulfamoyl)-2-pyridinone

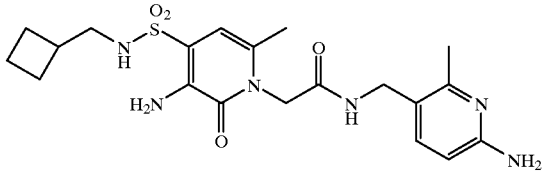

Step A: 4-Chloro-2-hydroxy-3-nitropyridine

Phosphorous oxychloride (63.4 mL, 0.68 mol) was added dropwise to a stirred mixture of 2,4-dihydroxy-3-nitropyridine (28.92 g, 0.17 mol) and benzyl triethylammonium chloride (155 g, 0.68 mol) in acetonitrile (560 mL). The reaction mixture was warmed to 60° C. for 1 h then was heated to reflux for 1 h. The reaction was cooled and the volatiles were evaporated in vacuo. An ice/water slurry (500 mL) was added to the residual oil and the mixture was stirred for 3 h at 0° C. The solids were collected by filtration, washing with water and hexanes to give the title compound as a solid;

NMR ($CD_3OD$); d 2.33 (s, 3H), 6.39 (s, 1H).

Step B: 4-Chloro-1-ethyloxycarbonylmethyl-3-nitro-2-pyridinone

Sodium hydride (60% dispersion in mineral oil, 7.5 g, 0.188 mol) was added to a stirred solution of 4-chloro-2-hydroxy-3-nitropyridine (23.68 g, 0.126 mol) in THF (250 mL) at 0° C. After 25 min ethyl bromoacetate (16.7 mL, 0.151 mol) was added and the reaction was warmed to 60° C. After 20 h the reaction was cooled and washed with brine acidified with 1M HCl. The organic layer was dried ($Na_2SO_4$) and evaporated in vacuo to a solid which was recrystallised from ethyl acetate/hexanes to give the title compound;

NMR ($CD_3OD$); d 1.29 (t, 3H), 2.43 (s, 3H), 4.25 (q, 2H), 4.92 (s, 2H), 6.57 (s, 1H).

Step C: 4-(2-Benzothiazinylmercaptyl)-1-ethyloxycarbonylmethyl-3-nitro-2-pyridinone Triethylamine (10.38 mL, 74.5 mmol) was added to a stirred solution of 4-chloro-1-ethyloxycarbonylmethyl-3-nitro-2-pyridinone (9.3 g, 33.86 mmol) and 2-mercaptobenzothiazole (6.23 g, 37.25 mmol) in ethanol (200 mL) and the reaction was heated to reflux. After 15 min the reaction was cooled and the volatiles were evaporated in vacuo. The residue was partitioned between chloroform and 1M HCl solution. The organic layer was dried ($Na_2SO_4$) and evaporated in vacuo to a solid which was triturated with 1:1 methanol/hexanes to give the title compound as a pale yellow solid;

NMR ($CDCl_3$); d 1.30 (t, 3H), 2.22 (s, 3H), 4.25 (q, 2H), 4.79 (s, 2H), 5.99 (s, 1H), 7.55 (m, 2H), 7.95 (d, 1H), 8.16 (d, 1H).

Step D: 3-Amino-4-(2-benzothiazinylmercaptyl)-1-ethyloxycarbonylmethyl-2-pyridinone A mixture of 4-(2-benzothiazinylmercaptyl)-1-ethyloxycarbonylmethyl-3-nitro-2-pyridinone (12.5 g, 30.83 mmol) and 10% palladium on carbon (6.25 g) was stirred as a suspension in ethyl acetate (400 mL) under hydrogen. After 16 h, the mixture was filtered through celite and evaporated in vacuo to give the title compound as a solid;

NMR ($CDCl_3$); d 1.33 (t, 3H), 2.25 (s, 3H), 4.28 (q, 2H), 4.85 (s, 2H), 4.98 (br s, 2H), 6.24 (s, 1H), 7.30 (t, 1H), 7.42 (t, 1H), 7.70 (d, 1H), 7.89 (d, 1H).

Step E: 4-(2-Benzothiazinylmercaptyl)-3-(N,N-Di-t-butoxycarbonylamino)-1-ethyloxycarbonylmethyl-2-pyridinone DMAP (3.1 g, 25.35 mmol) was added to a stirred solution of 3-amino-1-ethyloxycarbonylmethyl-4-(2-benzothiazinylmercaptyl)-2-pyridinone (8.66 g, 23.05 mmol) and di-t-butyldicarbonate (17.6 g, 80.66 mmol) in methylene chloride (60 mL). After 16 h, more di-t-butyldicarbonate (5.03 g) was added and the reaction was stirred for a further 3 h. The reaction was diluted with methylene chloride and was washed with 10% citric acid solution, dried (Na$_2$SO$_4$) and evaporated in vacuo. The residue was triturated with hot ethyl acetate/hexanes to give the title compound as a solid;

NMR (CDCl$_3$); d 1.29 (t, 3H), 1.47 (s, 18H), 2.21 (s, 3H), 4.23 (q, 2H), 4.78 (s, 2H), 6.10 (s, 1H), 7.44 (t, 1H), 7.53 (t, 1H), 7.84 (d, 1H), 8.07 (d, 1H).

Step F: 4-(2-benzothiazinylsulfonyl)-3-(N,N-di-t-pyridinone

A solution of potassium permanganate (10.6 g, 67.31 mmol) in water (90 mL) was added to a stirred solution of 4-(2-benzothiazinylmercaptyl)-3-(N,N-di-t-butoxycarbonylamino)-1-ethyloxycarbonylmethyl-2-pyridinone (9.686 g, 16.83 mmol) in 4:1 acetic acid/water (250 mL). After 62 h, the reaction was partitioned between ethyl acetate and 10% sodium sulfite solution. The organic layer was washed with 10% sodium sulfite solution, water (2×), sodium hydrogen carbonate solution (2×), water and brine, dried (Na$_2$SO$_4$) and evaporated in vacuo to a solid. This was triturated with ether to give the title compound as a solid;

NMR (CDCl$_3$); d 1.15 (s, 18H), 1.28 (t, 3H), 2.45 (s, 3H), 4.21 (q, 2H), 4.79 (s, 2H), 6.94 (s, 1H), 7.60 (m, 2H), 8.01 (d, 1H), 8.21 (d, 1H).

Steps G,H: 4-Chlorosulfonyl-3-(N,N-di-t-butoxycarbonylamino)-1-ethyloxycarbonylmethyl-2-pyridinone Zinc powder (6.93 g, 106 mmol) was added to a stirred mixture of 4-(2-benzothiazinylsulfonyl)-3-(N,N-di-t-butoxycarbonylamino)-1-ethyloxycarbonylmethyl-2-pyridinone (3.94 g, 6.48 mmol) and acetic acid (8.73 mL) in ethanol (63 mL). After 16 h, the reaction mixture was filtered and evaporated in vacuo at rt. NCS (0.952 g, 7.13 mmol) was added to a stirred mixture of this residue in methylene chloride (100 mL) at −5° C. After 15 min the reaction was warmed to rt and after a further 40 min the reaction was filtered through celite and evaporated in vacuo to give the title compound contaminated with benzothiazole (1 equivalent) as a yellow solid;

NMR (CDCl$_3$); d 1.31 (t, 3H), 1.44 (s, 18H), 2.42 (s, 3H), 4.26 (q, 2H), 4.83 (s, 2H), 6.57 (s, 1H).

Steps I,J: 3-Amino-4-(N-cyclobutylmethylsulfamoyl)-1-ethoxycarbonylmethyl-2-pyridinone NMM (1.43 mL, 13.0 mmol) was added to a stirred mixture of 4-chlorosulfonyl-3-(N,N-di-t-butoxycarbonylamino)-1-ethyloxycarbonylmethyl-2-pyridinone (as a mixture from Step H, 0.84 g) and cyclobutylmethylamine hydrochloride (348 mg, 2.86 mmol) in methylene chloride (15 mL). After 16 h the reaction was diluted with methylene chloride and washed with 10% citric acid solution. The organic layer was dried (Na$_2$SO$_4$) and evaporated. The residue was purified by flash column chromatography on silica (40% ethyl acetate/hexanes). HCl gas was bubbled through a stirred solution of the resulting compound in ethyl acetate (10 mL) at 0° C. for 15 min. The reaction was warmed to rt and after a further 3 h it was evaporated to give the title compound as a solid;

NMR (CDCl$_3$); d 1.30 (t, 3H), 1.64 (m, 2H), 1.88 (m, 2H), 2.04 (m, 2H), 2.24 (s, 3H), 2.44 (m, 1H), 2.99 (t, 2H), 4.25 (q, 2H), 4.68 (br t, 1H), 4.79 (s, 2H), 6.26 (s, 1H).

Step K: 3-Amino-1-carboxymethyl-4-(N-cyclobutylmethylsulfamoyl)-2-pyridinone

Lithium hydroxide hydrate (40 mg, 0.952 mmol) was added to a stirred solution of 3-amino-4-(N-cyclobutylmethylsulfamoyl)-1-ethoxycarbonylmethyl-2-pyridinone (170 mg, 0.476 mmol) in 1:3:3 water/methanol/THF (14 mL). After 2 h, the reaction was acidified with 1M HCl and the mixture was partitioned between chloroform and brine. The organic layer was dried (Na$_2$SO$_4$) and evaporated to give the title compound as a solid;

NMR (DMSO-d$_6$); d 1.59 (m, 2H), 1.73 (m, 2H), 1.90 (m, 2H), 2.17 (s, 3H), 2.34 (m, 1H), 2.77 (t, 2H), 4.71 (s, 2H), 5.93 (s, 2H), 6.16 (s, 1H), 7.68 (br t, 2H).

Step L: 3-Amino-1-(2-amino-6-methyl-5-methylenecarboxamidomethylpyridinyl)-4-(N-cyclobutylmethylsulfamoyl)-2-pyridinone EDC.HCl (85 mg, 0.444 mmol) was add to a stirred solution of 3-amino-1-carboxymethyl-4-(N-cyclobutylmethylsulfamoyl)-2-pyridinone (121.9 mg, 0.37 mmol), 2-amino-5-aminomethyl-6-methylpyridine dihydrochloride (93 mg, 0.444 mmol), HOBT (60 mg, 0.444 mmol), and NMM (0.24 mL, 2.22 mmol) in DMF (2.5 mL). After 16 h, the reaction was partitioned between ethyl acetate and water. The organic layer was washed with water and brine, dried (Na$_2$SO$_4$) and evaporated to a solid. The crude product was recrystallized from methylene chloride to give the title compound as a pale yellow crystalline solid;

NMR (DMSO-d$_6$); d 1.60 (m, 2H), 1.77 (m, 2H), 1.91 (m, 2H), 2.14 (s, 3H), 2.22 (s, 3H), 2.35 (m, 1H), 2.86 (d, 2H), 4.10 (d, 2H), 4.65 (s, 2H), 5.72 (s, 2H), 5.90 (s, 2H), 6.13 (s, 1H), 6.22 (d, 1H), 7.19 (d, 1H), 7.65 (br t, 2H), 8.43 (br t, 1H). HRMS (FAB) C$_{20}$H$_{29}$N$_6$O$_4$S calcd. 449.1966 (M+1)$^+$. Found: 449.1975.

EXAMPLE 4

Preparation of 6-(2-Amino-6-methyl-5-methylenecarbox-amidomethylpyridinyl)-7-methyl-5-oxo-2-cyclobutylmethyl-3,4,5,6-tetrahydropyrido-[3,4-e]-1,2,4-thiazine-1,1-dioxide:

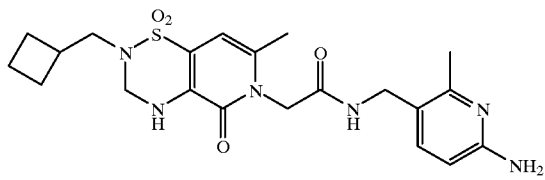

A stirred suspension of 3-amino-1-(2-amino-6-methyl-5-methylenecarboxamidomethylpyridinyl)-4-(N-cyclobutylmethylsulfamoyl)-2-pyridinone (30 mg, 0.067 mmol), 37% aqueous formaldehyde (0.1 mL) and 14.8M ammonium hydroxide (0.018 mL) in 2:1 ethanol/water (1.5 mL) was warmed to reflux. After 6 h the reaction was cooled and water was added to give a precipitate which was collected by filtration, washing with water. The solids were dissolved in warm 1M HCl and the solution was then left to stand at rt. The resulting precipitate was collected by filtration to give the title compound as a crystalline solid;

NMR (DMSO-d$_6$); d 1.66 (m, 2H), 1.81 (m, 2H), 1.99 (m, 2H), 2.16 (s, 3H), 2.42 (s, 3H), 2.86 (d, 2H), 4.14 (d, 2H), 4.65 (s, 2H), 4.75 (s, 2H), 6.25 (s, 1H), 6.79 (d, 1H), 6.98 (br s, 1H), 7.65 (br s, 2H), 7.75 (d, 1H), 8.74 (br t, 1H). HRMS (FAB) C$_{21}$H$_{29}$N$_6$O$_4$S calcd. 461.1966 (M+1)$^+$. Found: 461.1956.

EXAMPLE 5

Preparation of 3-Amino-1-(2-amino-6-methyl-5-methylenecarboxamidomethylpyridinyl)-4(N-cyclobutylsulfamoyl)-2-pyridinone

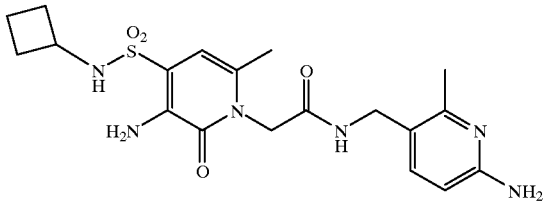

The title compound was prepared from 4-chlorosulfonyl-3-(N,N-di-t-butoxycarbonylamino)-1-ethyloxycarbonylmethyl-2-pyridinone and cyclobutylamine using the procedures of Example 3, Steps I–L as a crystalline solid;

HRMS (FAB) $C_{19}H_{27}N_6O_4S$ calcd. 435.1809 $(M+1)^+$. Found: 435.1802.

EXAMPLE 6

Preparation of 6-(2-Amino-6-methyl-5-methylenecarboxamido-methylpyridinyl)-7-methyl-5-oxo-2-cyclobutyl-3,4,5,6-tetrahydropyrido-[3,4-e]-1,2,4-thiazine-1,1-dioxide

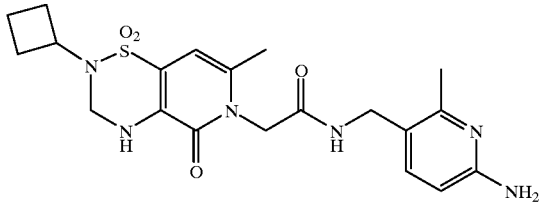

The HCl salt of the title compound was prepared from 3-amino-1-(2-amino-6-methyl-5-methylenecarboxamidomethylpyridinyl)-4-(N-cyclobutylsulfamoyl)-2-pyridinone using the procedure of Example 4, as a crystalline solid;

HRMS (FAB) $C_{20}H_{27}N_6O_4S$ calcd. 447.1809 $(M+1)^+$. Found: 447.1803.

EXAMPLE 7

Preparation of 3-amino-1-(2-amino-6-methyl-5-methylenecarboxamidomethylpyridinyl)-4-(N-cyclopropylsulfamoyl)-2-pyridinone

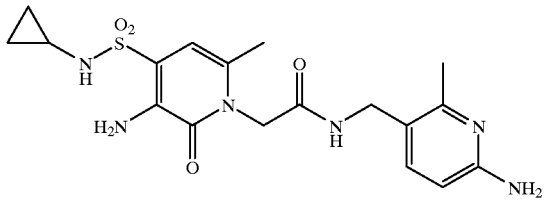

The title compound was prepared from 4-chlorosulfonyl-3-(N,N-di-t-butoxycarbonylamino)-1-ethyloxycarbonylmethyl-2-pyridinone and cyclopropylamine using the procedure of Example 3, Steps I–L as a crystalline solid;

HRMS (FAB) $C_{18}H_{25}N_6O_4S$ calcd. 421.1653 $(M+1)^+$. Found: 421.1643.

EXAMPLE 8

Preparation of 6-(2-Amino-6-methyl-5-methylenecarbox-amidomethylpyridinyl)-7-methyl-5-oxo-2-cyclopropyl-3,4,5,6-tetrahydropyrido-[3,4-e]-1,2,4-thiazine-1,1-dioxide

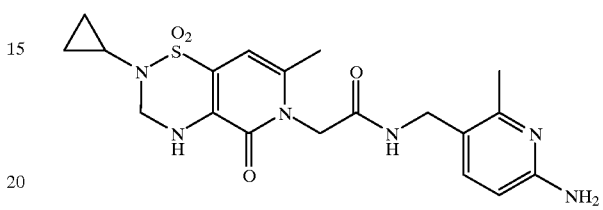

A stirred solution of 3-amino-1-carboxymethyl-4-(N-cyclopropylsulfamoyl)-2-pyridinone (0.26 mmol, prepared from 4-chlorosulfonyl-3-(N,N-di-t-butoxycarbonylamino)-1-ethyloxycarbonylmethyl-2-pyridinone and cyclopropylamine using the procedure of Example 3, Steps I–K), 37% aqueous formaldehyde (0.2 mL) and 14.8M ammonium hydroxide (0.036 mL) in 2:1 ethanol/water (1.5 mL) was warmed to reflux. After 1.5 h the reaction was cooled and evaporated in vacuo. The residue was partitioned between THF and brine, acidified with HCl and the organic layer was dried ($Na_2SO_4$) and evaporated to a solid. EDC.HCl (60 mg, 0.312 mmol) was added to a stirred solution of this material, 2-amino-5-aminomethyl-6-methylpyridine dihydrochloride (66 mg, 0.312 mmol), HOBT (42 mg, 0.312 mmol), and NMM (0.17 mL, 1.56 mmol) in DMF (3.0 mL). After 16 h, the reaction was partitioned between ethyl acetate and water. The organic layer was washed with brine, dried ($Na_2SO_4$) and evaporated to a solid. The crude product was purified by flash column chromatography on silica gel (3–8 % methanol/chloroform gradient) and then triturated with methanol to give the title compound as a crystalline solid;

HRMS (FAB) $C_{19}H_{25}N_6O_4S$ calcd. 433.1658 $(M+1)^+$. Found: 433.1651.

EXAMPLE 9

Preparation of 3-amino-1-(2-amino-6-methyl-5-methylenecarboxamidomethylpyridinyl)-4-pyrrolidinylsulfamoyl-2-pyridinone

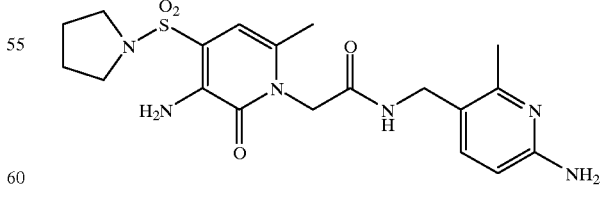

The HCl salt of the title compound was prepared from 4-chlorosulfonyl-3-(N,N-di-t-butoxycarbonylamino)-1-ethyloxycarbonylmethyl-2-pyridinone and cyclopropylamine using the procedure of Example 3, Steps I–L as a crystalline solid;

HRMS (FAB) $C_{19}H_{27}N_6O_4S$ calcd. 435.1815 (M+1)$^+$. Found: 435.1817.

EXAMPLE 10

Preparation of 3-Amino-1-(2-amino-6-methyl-5-methylenecarboxamidomethylpyridinyl)-4-(N-cyclopropylmethylsulfamoyl)-2-pyridinone

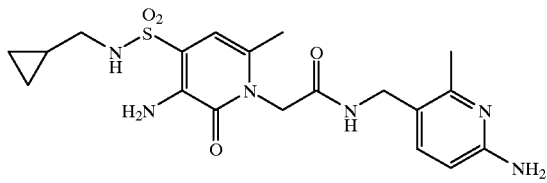

The TFA salt of the title compound was prepared from 4-chlorosulfonyl-3-(N,N-di-t-butoxycarbonylamino)-1-ethyloxycarbonylmethyl-2-pyridinone and cyclopropylmethylamine using the procedure of Example 3, Steps I–L followed by preparative HPLC (acetonitrile/0.1% aqueous TFA gradient), as a solid;

HRMS (FAB) $C_{19}H_{27}N_6O_4S$ calcd. 435.1815 (M+1)$^+$. Found: 435.1817.

EXAMPLE 11

Preparation of 6-(2-Amino-6-methyl-5-methylenecarbox-amidomethylpyridinyl)-7-methyl-5-oxo-2-cyclopropylmethyl-3,4,5,6-tetrahydropyrido-[3,4-e]-1,2,4-thiazine-1,1-dioxide:

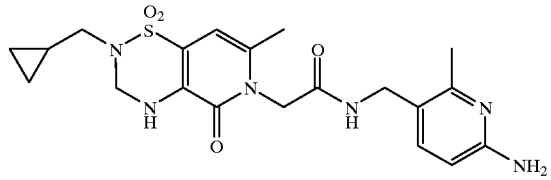

The TFA salt of the title compound was prepared from 4-chlorosulfonyl-3-(N,N-di-t-butoxycarbonylamino)-1-ethyloxycarbonylmethyl-2-pyridinone and cyclopropylmethylamine using the procedure of Example 8, followed by preparative HPLC (acetonitrile/0.1% aqueous TFA gradient), as a solid;

HRMS (FAB) $C_{20}H_{27}N_6O_4S$ calcd. 447.1814 (M+1)$^+$. Found: 447.1823.

EXAMPLE 12

Tablet Preparation

Tablets containing 25.0, 50.0, and 100.0 mg., respectively, of the following active compounds are prepared as illustrated below (compositions A–I). Active I is 3-amino-1-(2-amino-6-methyl-5-methylenecarboxamidomethylpyridinyl)-4-(N-cyclobutylmethyl-sulfamoyl)-2-pyridinone; Active II is 6-(2-Amino-6-methyl-5-methylenecarboxamidomethylpyridinyl)-7-methyl-5-oxo-2-cyclobutylmethyl-3,4,5,6-tetrahydropyrido-[3,4-e]-1,2,4thiazine-1,1-dioxide; Active III is 3-Amino-1-(2-amino-6-methyl-5-methylene-carboxamidomethylpyridinyl)-4-(N-cyclobutylsulfamoyl)-2-pyridinone; and Active IV is 3-amino-1-(2-amino-6-methyl-5-methylene-carboxamidomethylpyridinyl)-4-pyrrolidinylsulfamoyl-2-pyridinone.

TABLE FOR DOSES CONTAINING FROM 25–100 MG OF THE ACTIVE COMPOUND

| Component | Amount-mg | | | | | | | | |
|---|---|---|---|---|---|---|---|---|---|
| | A | B | C | D | E | F | G | H | I |
| Active I | 25 | 50 | 100 | — | — | — | — | — | — |
| Active II | — | — | — | 25 | 50 | 100 | — | — | — |
| Active III | — | — | — | — | — | — | 25 | 50 | 100 |
| Microcrystalline cellulose | 37.25 | 100 | 200 | 37.25 | 100 | 200 | 37.25 | 100 | 200 |
| Modified food corn starch | 37.25 | 4.25 | 8.5 | 37.25 | 4.25 | 8.5 | 37.25 | 4.25 | 8.5 |
| Magnesium stearate | 0.5 | 0.75 | 1.5 | 0.5 | 0.75 | 1.5 | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 13

Tablet Preparation

Exemplary compositions 3-amino-1-(2-amino-6-methyl-5-methylenecarboxamidomethylpyridinyl)-4-(N-cyclobutylmethylsulfamoyl)-2-pyridinone tablets are shown below:

| Component | 0.25 mg | 2 mg | 10 mg | 50 mg |
|---|---|---|---|---|
| Active IV | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation via Direct Compression

Active IV, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation via Dry Granulation

Alternatively, a dry powder blend is compacted under modest forces and remilled to afford granules of specified particle size. The granules are then mixed with magnesium stearate and tabletted as stated above.

EXAMPLE 14

Intravenous Formulations

Intravenous formulations of 3-amino-1-(2-amino-6-methyl-5-methylenecarboxamidomethylpyridinyl)-4-(N-cyclobutylmethylsulfamoyl)-2-pyridinone were prepared according to general intravenous formulation procedures.

| Component | Estimated range |
|---|---|
| Active IV | 0.12–0.61 mg |
| D-glucuronic acid* | 0.5–5 mg |
| Mannitol NF | 50–53 mg |
| Water for injection | q.s. 1.0 mL |

1N sodium hydroxide is used to achieve a solution pH in the range of between 3.9–4.1.

Exemplary compositions A–C are as follows:

| Component | A | B | C |
|---|---|---|---|
| Active IV | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base;
**0.25 mg free base;
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:

1. A compound having the formula:

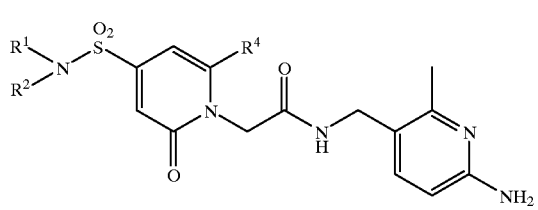

I or a pharmaceutically acceptable salt thereof, wherein
$R^1$ and $R^2$ are independently selected from
hydrogen,
-phenyl, unsubstituted or substituted with one or more of
$C_{1-4}$ alkyl,
$C_{1-4}$ alkoxy,
halogen,
hydroxy,
COOH, or
$CONH_2$,
naphthyl,
biphenyl,
a 5- to 7-membered mono- or a 9- to 10-membered bicyclic heterocyclic ring which can be saturated or unsaturated, and which contains from one to four heteroatoms selected from the group consisting of N, O and S,
—$C_{1-7}$ alkyl, unsubstituted or substituted with one or more of
hydroxy,
COOH,
amino,
aryl,
$C_{3-7}$ cycloalkyl,
—$CF_3$
$C_{3-7}$ cycloalkyl,
$C_{7-12}$ bicyclic alkyl, or
$C_{10-16}$ tricyclic alkyl;
or $R^1$ and $R^2$ together with the nitrogen to which they are bound form a 5- or 6-membered ring containing 1 nitrogen atom;
$R^4$ is hydrogen,
—$C_{1-4}$ alkyl,
$C_{3-7}$ cycloalkyl, or
trifluoromethyl.

2. A compound of claim 1, or a pharmaceutically acceptable salt thereof, wherein $R^1$ is hydrogen; $R^2$ is —$C_{3-7}$ cycloalkyl or —$CH_2$ $C_{3-7}$ cycloalkyl; or $R^1$ and $R^2$ form a 5- or 6-membered ring containing 1 nitrogen atom; and $R^4$ is hydrogen, —$C_{1-4}$ alkyl, $C_{3-7}$ cycloalkyl or trifluoromethyl.

3. A compound of claim 2, or a pharmaceutically acceptable salt thereof, selected from the group consisting of

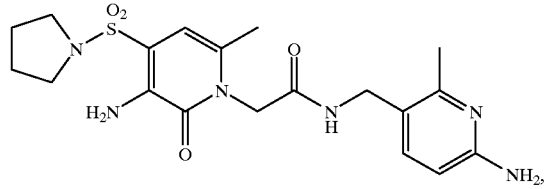

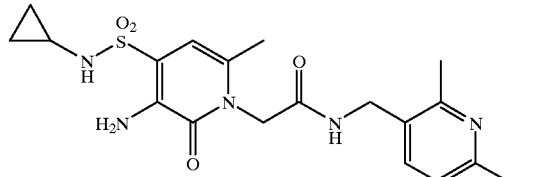

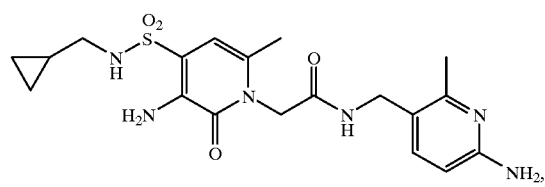

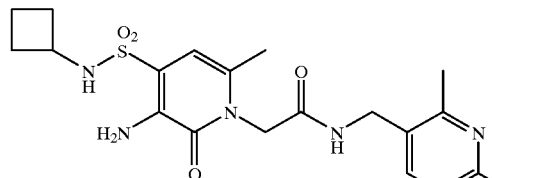

-continued

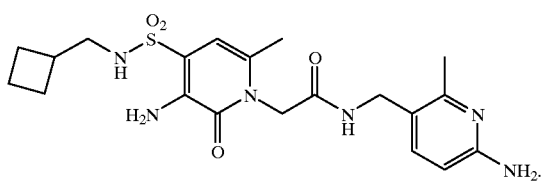

4. A pharmaceutical composition for inhibiting thrombus formation comprising a therapeutically effective amount of a compound of claim 1 or a pharmaceutically acceptable salt thereof and a pharmaceutically acceptable carrier.

5. A method for inhibiting thrombus formation in blood comprising adding to the blood an effective amount of a composition of claim 4.

6. A method of inhibiting thrombus formation in blood in a mammal comprising administering to the mammal an effective amount of a composition of claim 4.

* * * * *